US 6,509,505 B1

(12) United States Patent
Paciello et al.

(10) Patent No.: US 6,509,505 B1
(45) Date of Patent: *Jan. 21, 2003

(54) PHOSPHABENZENE COMPOUNDS AND THEIR USE IN HYDROFORMYLATION

(75) Inventors: Rocco Paciello, Bad Dürkheim (DE); Thomas Mackewitz, Mannheim (DE); Michael Röper, Wachenheim (DE); Bernhard Breit, Schriesheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/936,346
(22) PCT Filed: Mar. 15, 2000
(86) PCT No.: PCT/EP00/02288
§ 371 (c)(1), (2), (4) Date: Sep. 11, 2001
(87) PCT Pub. No.: WO00/55164
PCT Pub. Date: Sep. 21, 2000

(30) Foreign Application Priority Data

Mar. 17, 1999 (DE) .......................... 199 11 920

(51) Int. Cl.$^7$ .................................. C07F 9/50
(52) U.S. Cl. .................... 568/12; 568/451; 568/454
(58) Field of Search .............. 568/12, 451, 454; 556/13

(56) References Cited

U.S. PATENT DOCUMENTS 6,252,117 B1 * 6/2001 Mackewitz et al. .......... 568/12
6,255,532 B1 * 7/2001 Paciello et al. ............. 568/12

FOREIGN PATENT DOCUMENTS

DE 1618 668 2/1971
DE 1 688 416 8/1971
WO 97/46507 12/1997

OTHER PUBLICATIONS

WO 99/16774 by Paciello et al Apr./1999.*
Derwent Abst. DE 196 21 967 (1997).
* cited by examiner Primary Examiner—Jean F. Vollano
(74) Attorney, Agent, or Firm—Keil & Weinkauf

(57) ABSTRACT

Phosphabenzene compounds of the formula (I)

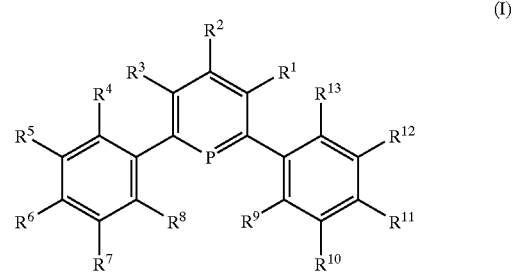

where the radicals $R^1$ to $R^{13}$ are, independently of one another, hydrogen, COOM, $SO_3M$, $NR_3X$, $NR_2$, OR, COOR or SR (where M=hydrogen, $NH_4$ or alkali metal, X=anion, R=hydrogen or $C_1$–$C_6$-alkyl), or $C_1$–$C_{12}$-alkyl, $C_6$–$C_{12}$-aryl, $C_7$–$C_{12}$-aralkyl, $C_7$–$C_{12}$-alkaryl or $C_3$–$C_6$-heteroaromatics, where the alkyl, aryl, alkaryl and aralkyl radicals may bear the abovementioned radicals as substituents and two or more of the radicals may be joined to form aliphatic or fused-on rings, where at least one of the radicals $R^4$ and $R^8$ and at least one of the radicals $R^9$ and $R^{13}$ is not hydrogen, can be used for preparing hydroformylation catalysts.

9 Claims, No Drawings

PHOSPHABENZENE COMPOUNDS AND THEIR USE IN HYDROFORMYLATION

This application is a 371 of PCT/EP00/02288 filed Mar. 15, 2000, now WO 00/55164.

The present invention relates to phosphabenzene compounds and their use in complexes of transition metals of transition group VIII of the Periodic Table of the Elements in the preparation of aldehydes by hydroformylation of olefins using $CO/H_2$ at up to 200° C. and pressures of up to 700 bar.

Hydroformylation is a known process utilized industrially for the preparation of aldehydes from olefins, carbon monoxide and hydrogen. As described in WO 97/46507, phosphabenzenes are active cocatalysts for the hydroformylation of olefins. This document describes a process for preparing aldehydes by hydroformylation of olefins using $CO/H_2$ in the presence of complexes containing phosphabenzene compounds as ligands.

However, the phosphabenzene compounds used, for example 2,4,6-triphenylphosphabenzene and 2,6-bis(2-naphthyl)-4-phenylphosphabenzene, but also phosphabenzenes such as 2,3,5,6-tetraphenylphosphabenzene or 2,3,4,5,6-pentaphenylphosphabenzene, have the disadvantage that they can be degraded under hydroformylation conditions by partial or complete hydrogenation of the phosphabenzene system and subsequent addition reactions (see Examples 11–14). This forms, inter alia, secondary and tertiary phosphines which greatly inhibit the hydroformylation activity of the catalyst system.

Similar phosphabenzene compounds are described in DE-A-19 621 967 and DE-A-16 68 416.

It is an object of the present invention to provide phosphabenzene ligands which avoid the disadvantages of the known ligands.

We have found that this object is achieved by phosphabenzene compounds of the formula (I)

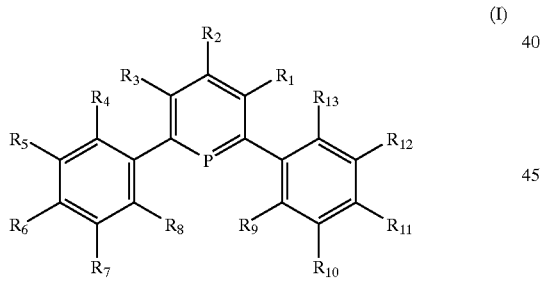

(I)

where the radicals $R^1$ to $R^{13}$ are, independently of one another, hydrogen, COOM, $SO_3M$, $NR_3X$, $NR_2$, OR, COOR or SR (where M=hydrogen, $NH_4$ or alkali metal, X=anion, R=hydrogen or $C_1$–$C_6$-alkyl), or $C_1$–$C_{12}$-alkyl, $C_6$–$C_{12}$-aryl, $C_7$–$C_{12}$-aralkyl, $C_7$–$C_{12}$-alkaryl or $C_3$–$C_6$-heteroaromatics, where the alkyl, aryl, alkaryl and aralkyl radicals may bear the abovementioned radicals as substituents and two or more of the radicals may be joined to form aliphatic or fused-on rings, where at least one of the radicals $R^4$ and $R^8$ and at least one of the radicals $R^9$ and $R^{13}$ is not hydrogen.

Preferably, at least one of the radicals $R^4$ and $R^8$ and at least one of the radicals $R^9$ and $R^{13}$ are, independently of one another, $C_1$–$C_{12}$-alkyl, $C_6$–$C_{12}$-aryl, $C_7$–$C_{12}$-aralkyl or $C_7$–$C_{12}$-alkaryl, or $R^4$ and $R^3$ and/or $R^{13}$ and $R^1$ form a $C_2$–$C_4$-alkylene radical.

Particularly preferably, at least one of the radicals $R^4$ and $R^8$ and at least one of the radicals $R^9$ and $R^{13}$ are $C_1$–$C_6$-alkyl, or ($R^4$ and $R^3$) and ($R^{13}$ and $R^1$) in each case form a $C_2$–$C_3$-alkylene radical.

$R^2$ is preferably a phenyl radical which may be substituted by from 1 to 5, preferably from 1 to 3, in particular 1 or 2, $C_1$–$C_6$-alkyl radicals.

Particularly preferably, the radicals $R^1$ and $R^3$ are hydrogen and in each case at most three of the radicals $R^4$ to $R^8$ and $R^9$ to $R^{13}$ are not hydrogen. The radicals $R^4$ to $R^8$ and $R^9$ to $R^{13}$ in each case particularly preferably have a maximum of 6, in particular a maximum of 3, carbon atoms. In particular, the phosphobenzene compounds of the formula (I) have no atoms apart from the one phosphorus atom which are not carbon or hydrogen.

The compounds of the formula (I) preferably contain, in addition to the phosphobenzene ring, from 3 to 5, in particular 3, further aromatic rings. The number of alkyl radicals in the compounds of the formula (I) is preferably 0 in the case of purely cyclic structures, otherwise preferably from 2 to 7, in particular from 2 to 6. The alkyl radicals can be linear or branched. Preferably, only linear alkyl radicals are present. The same applies analogously to bridging alkylene groups.

Examples of phosphobenzenes which may be mentioned are:

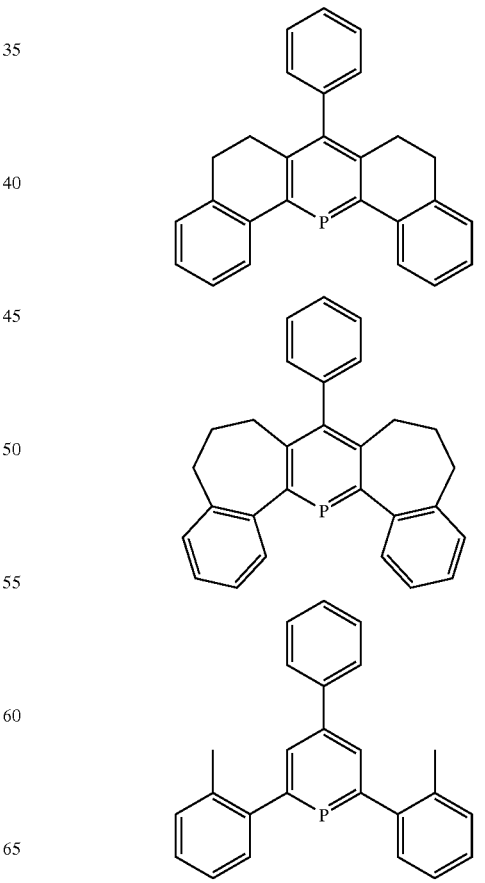

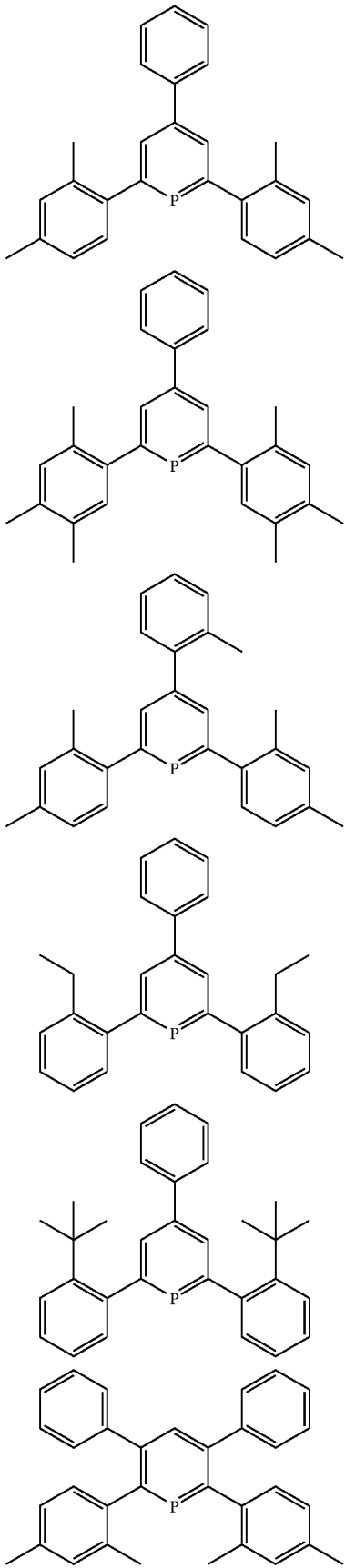

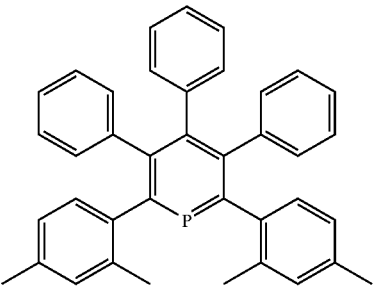

It has been found that, in particular, the introduction of 2-alkylaryl substituents in the 2 and 6 positions of the phosphobenzene system gives a significantly increased stability of the cocatalyst under hydroformylation conditions and the catalyst systems display comparable activities to those of corresponding unsubstituted systems.

The degradation of phosphobenzene compounds having 2-alkylaryl substituents in the 2 and 6 positions of the phosphobenzene system under hydroformylation conditions is significantly reduced compared to analogous systems bearing unsubstituted aryl substituents.

The principle of the preparation of the phosphobenzenes is known. General synthetic methods may be found in G. Märkl in Multiple Bonds and Low Coordination in Phosphorus Chemistry (Editors M. Regitz, O. J. Scherer), Thieme, Stuttgart, 1990, pp. 220 to 257 (and the references cited therein). Processes for preparing phosphobenzene compounds from pyrylium salts by reaction with phosphine are described in WO 97/46507, DE-A-196 21 967 and the earlier-priority DE-A-197 43 197 which is not a prior publication.

The preparation is preferably carried out by reacting corresponding pyrylium salts with $PH_3$ in the presence or absence of a catalytic amount of acid or base and in the presence or absence of a solvent or diluent. The pyrylium salts are preferably brought into contact with $PH_3$ at above 0° C. and reacted at from 0° C. to 200° C. and a pressure above 1 bar.

It has been found, according to the present invention, that phosphobenzene compounds of the formula above are obtainable by reaction of the corresponding pyrylium salts, i.e. compounds in which the phosphorus in the formula is replaced by $O^+$ together with a corresponding counterion, with $PH_3$ if particular process conditions are adhered to. The pyrylium salts are commercially available or can be prepared by simple means. $PH_3$ is commercially available.

The reaction is preferably carried out at a $PH_3$ partial pressure in the range from 0.1 to 100 bar, particularly preferably from 5 to 35 bar, in particular from 20 to 30 bar. The total pressure in the system depends on the solvent employed. The total pressure can be increased by injection of $PH_3$ or inert gas.

$PH_3$ is preferably passed into the reaction mixture during the reaction in order to keep the $PH_3$ partial pressure essentially constant. This procedure allows a particularly economical and rapid reaction to form the desired phosphobenzene compounds. High product purities and conversions are achieved. The process of the present invention can be used reliably for many products. It can be carried out continuously or batchwise, preferably batchwise. In a particularly advantageous process variant, the pyrylium salts are combined with $PH_3$ at ambient temperature, and the mixture obtained in this way is heated to from 60 to 140° C., preferably from 80 to 130° C., in order to bring about the reaction.

The reaction temperature is particularly preferably in the range from 100 to 120° C. The reaction is preferably carried out in an autoclave. In addition to $PH_3$, it is possible to make additional use of an inert gas by means of which the desired total pressure is set. However, preference is given to using only $PH_3$.

The reaction can be carried out in the presence or absence of a solvent or diluent. It is preferably carried out in the presence of a solvent or diluent. Suitable solvents or diluents are, for example, lower aliphatic alcohols such as methanol, ethanol, n-propanol, i-propanol, n-butanol, i-butanol, tert-butanol or pentanol isomers, preferably ethanol, propanol or butanols, in particular n-butanol.

The reaction can be carried out in the presence of an acid catalyst. Suitable acid catalysts are mineral acids such as HI, HCl, HBr. In particular, hydrogen bromide in acetic acid or acetic anhydride is used as acid catalyst. Preference is given to carrying out the reaction without an acid catalyst.

After the reaction, the reaction mixture is preferably depressurized and, if desired, purged with an inert gas. The gases given off from the reaction mixture are cooled to separate off unreacted $PH_3$ in liquid form and passed through a separator, and the $PH_3$ separated off is reused in the reaction.

In a particularly economical and ecologically acceptable variant of the process, $PH_3$ is passed into a reactor, the reaction is carried out, and the gas stream is passed via a further line through a cooler of any construction type in which the $PH_3$ is condensed out. In a downstream separator of any construction type, the $PH_3$ is then separated off and returned to the reaction, for example by means of a pump. In order to obtain a waste gas which is particularly low in $PH_3$, the use of a second, downstream cooler and separator is advantageous. In order to free the reactor gas space and the equipment used completely of $PH_3$, which is advantageous because of the toxicity of $PH_3$, a flushing line for flushing with an inert gas such as nitrogen should be provided. In this case, the flushing gas should be passed through the combination of cooler and separator.

The time required for the reaction depends on the type of pyrylium salt. Depending on the pyrylium salt, the reaction is preferably carried out for a period of from 1 to 4 hours. The amount of acid catalyst used is, based on the pyrylium salt, preferably from 0.01 to 1%, particularly preferably from 0.03 to 0.1%. In the reaction using a solvent, the concentration of $PH_3$ in the solvent depends on the $PH_3$ partial pressure and on the type of solvent; particularly when carrying out the reaction continuously, a high concentration of $PH_3$ in the solvent should be maintained.

To achieve high conversions in a short reaction time, high $PH_3$ pressures and continuous injection of further $PH_3$ are preferably employed.

Many different pyrylium salts can be used in the process of the invention. The process is generally not restricted to particular classes of compounds. For example, the pyrylium salts can be ferrates, zincates, chlorides, borates, with or without a $C_1$–$C_{16}$-alkyl radical, triflates, trifluoroacetates or preferably tetrafluoroborates, perchlorates, hydrogen sulfates, bromides, iodides or mixtures thereof. Preference is given to using tetrafluoroborates. The organic group of the pyrylium salts used according to the present invention is described in more detail below by means of the phosphobenzene compounds prepared therefrom.

This process allows the above compounds to be prepared. Compounds which have not yet been described in detail can be obtained analogously.

The activity of phosphobenzene compounds having 2-alkylaryl substituents in the 2 and 6 positions of the phosphobenzene system as cocatalyst in hydroformylation is comparable to analogous systems bearing unsubstituted aryl substituents (see WO 97/02757 and Examples 6, 7, 9 and 10).

The compounds of the present invention can be used for preparing complexes with metals of transition group VIII of the Periodic Table of the Elements. Such complexes can be used as (co)catalysts in hydroformylations of olefins using $CO/H_2$. Suitable reaction conditions are described in DE-A-196 21 967 and WO 97/02757.

The most effective catalysts are those of the formula $M(L)_n(CO)_m$ in which M is at least one central atom of an element of transition group VIII of the Periodic Table of the Elements, L is at least one ligand of the formula I, n and m are each at least 1 to 3 and the sum n+m is from 2 to 5, and further radicals such as hydrido or alkyl or acyl radicals may be present as ligands.

The active carbonyl complex is generally formed in situ, i.e. in the hydroformylation reactor, from a salt or compound of the metal M, the ligand and carbon monoxide, but it can also be prepared separately and used as such.

The catalyst complexes preferably comprise a central atom M selected from among the transition metals cobalt, ruthenium, rhodium, palladium and platinum, in particular cobalt and rhodium, complexed by carbonyl groups and hydrido, alkyl or acyl radicals and the preferred monodentate or polydentate phosphabenzenes to be used according to the present invention as ligands. If the catalyst complexes are produced in situ, simple precursor complexes such as biscarbonylrhodium acetylacetonate or rhodium acetate are exposed to the reaction conditions En the presence of the corresponding ligands, or precursor complexes are admixed with activating additives such as Bronsted or Lewis acids or Lewis bases.

To form the catalyst in situ in the reaction mixture, the ligand is used in a molar ratio (calculated as equivalents of phosphorus) to rhodium of from 1:1 to 1000:1 and an inert solvent is additionally used. Particularly preferred solvents are the aldehydes which are formed by reaction of the respective olefin, and also the high boilers intrinsic to the synthesis, which are formed by subsequent reactions of the respective aldehyde in the hydroformylation process. In the case of ligands which have been made hydrophilic by means of suitable substituents, preference is given to using water, alcohols or other polar solvents.

The composition of the synthesis gas $CO/H_2$ used in the hydroformylation process of the present invention can be varied within wide limits. For example, synthesis gas having $CO/H_2$ molar ratios of from 5:95 to 70:30 can be successfully used; preference is given to using synthesis gas having $CO/H_2$ ratios of from 40:60 to 60:40, particularly preferably about 1:1.

The hydroformylation reaction with CO and $H_2$ in the presence of the catalyst is carried out at from 0 to 200° C., preferably from 20 to 180° C., in particular from 50 to 150° C. However, an optimum temperature is advantageously determined by experiment for each catalyst system. Depending on the (co)catalyst, i.e. the ligand, and the substrate, the reaction pressure can vary in a range from atmospheric pressure to 700 bar, preferably up to 300 bar. Reactions in a range up to about 30 bar are normally referred to as low-pressure reactions, those in a range up to about 100 bar as intermediate-pressure reactions and those over 100 bar as high-pressure reactions.

In the hydroformylation reaction, the catalyst is generally homogeneously dissolved in the reaction medium and is separated from the reaction product and reused in the hydroformylation stage.

The process generally gives exclusively the corresponding aldehydes in excellent yields.

Olefins which can be hydroformylated according to the present invention are α-olefins or internal olefins or internal, branched olefins. Examples which may be mentioned are the following: ethylene, propene, 1-butene, 1-octene, $C_5$–$C_{20}$-α-olefins, linear $C_5$–$C_{20}$ internal olefins, 2-butene; branched, internal octene mixtures; branched, internal nonene mixtures; branched, internal dodecene mixtures, cyclohexene, α-pinene, styrene, 4-isobutylstyrene, methyl 3-pentenoate, methyl 4-pentenoate, methyl oleate, 3-pentenonitrile, 4-pentenonitrile, 2,7-octadien-1-ol, 7-octanal, methyl acrylate, methyl methacrylate, acrylonitrile, vinyl acetate, vinyl glycol diacetate, vinyl methyl ether, polypropene, polyisobutylene. Further suitable substrates are dienes or polyenes having isolated or conjugated double bonds. Examples are 1,3-butadiene, 1,5-hexadiene, vinylcyclohexene, dicyclopentadiene, 1,5,9-cyclooctatriene, butadiene homopolymers and copolymers, polyisobutene.

Otherwise, the hydroformylation reaction is carried out in a manner known per se. Details of the process conditions may be found in Belier et al., Journal of Molecular Catalysis A: 104 (1995) 17–85 and Falbe, Ed., New Syntheses with Carbon Monoxide, Springer, Berlin 1980, p. 55ff.

The invention is illustrated by the following examples:

EXAMPLE 1

Preparation of 2,6-bis (2,4-Dimethylphenyl)-4-phenylpyrylium Tetrafluoroborate

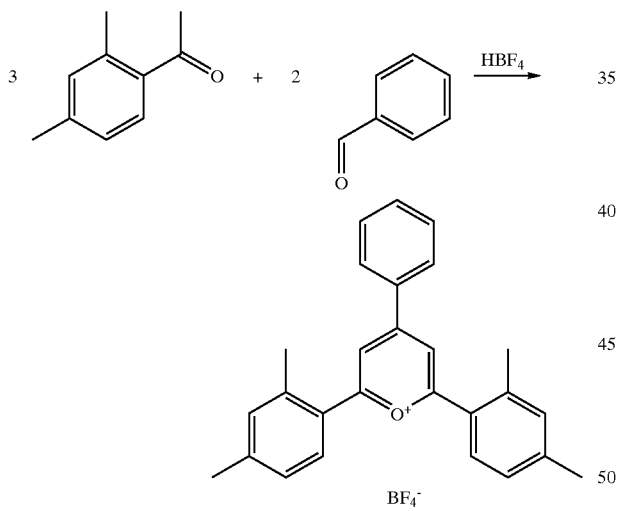

271 g (2.6 mol) of benzaldehyde and 542 g (3.7 mol) of 2,4-dimethylacetophenone were dissolved in 400 ml of 1,2-dichloroethane and heated to 80° C. 606 g (3.7 mol) of a 54% strength ether solution of tetrafluoroboric acid were slowly added dropwise to this solution while stirring. The mixture was subsequently stirred for another 4 hours at this temperature and was then allowed to cool to room temperature. The volatile constituents of the deep red solution obtained were distilled off in a high vacuum with slight warming. The residue was admixed with a toluene/water mixture (1:1).

The orange-yellow solid which precipitated was filtered off, washed with water and toluene and dried in a high vacuum. To recrystallize the crude product, the solid was suspended in methanol, and dichloromethane was subsequently added until a clear solution had been obtained. While warming gently, the solvent was distilled off in a high vacuum until solid precipitated again. The product was filtered off, washed in succession with methanol and n-pentane and subsequently dried in a high vacuum. Yield: 180 g (32%) of light-yellow solid.

General Experimental Description for Preparing Phosphabenzenes

All the following experiments (batchwise) were carried out in a 300 ml autoclave (material: HC). The autoclave was charged with the pyrylium salt and a suitable solvent and pressurized with 5 bar of nitrogen. The gas space was subsequently flushed with $PH_3$. The autoclave was pressurized with $PH_3$ to 5 bar at room temperature and further $PH_3$ was injected until the pressure remained constant at 5 bar. The reaction mixture was heated to 110° C. and the solution was stirred vigorously with a sparging stirrer. Further $PH_3$ was injected to a pressure of 30 bar. During the reaction, the pressure in the reactor was held at the desired level by injection of further $PH_3$ via a pressure regulator. After a reaction time of 4 hours, the autoclave was cooled, vented, thoroughly purged with nitrogen while stirring and the product was taken out. The autoclave product was then worked up as described below.

EXAMPLE 2

Preparation of 2,6-bis(2,4-Dimethylphenyl)-4-Phenylphosphabenzene

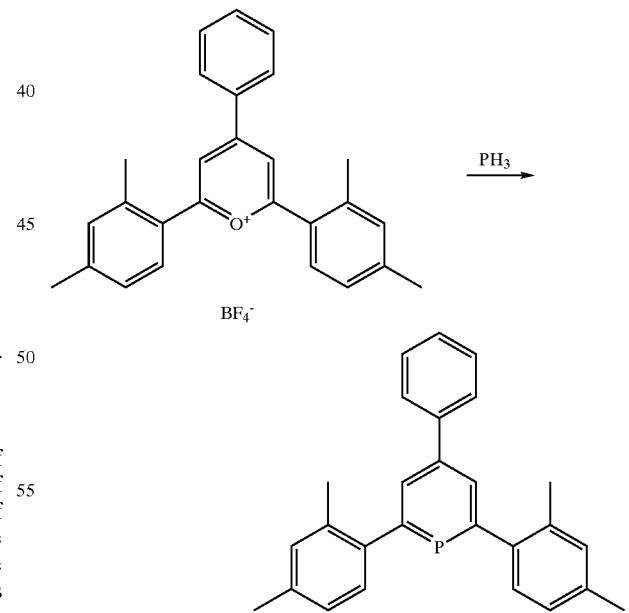

20 g (44 mmol) of 2,6-bis(2,4-dimethylphenyl)-4-phenylpyrylium tetrafluoroborate in 150 ml of n-butanol were used as starting material. The autoclave product obtained after the reaction with $PH_3$ was evaporated to half its volume under reduced pressure. The solid which precipi tated was filtered off with suction, washed with n-butanol and subsequently dissolved in toluene. The toluene solution was then washed with water until the aqueous phase was neutral. After removal of the solvent and washing with a little n-pentane, the residue was dissolved in 250 ml of diethyl ether/methanol (3:2). The solution obtained was evaporated under reduced pressure at about 30° C. until a solid precipitated. The solid was filtered off with suction, washed with a little methanol and n-pentane and subsequently dried in a high vacuum. Yield: 8.9 g (53%) of white solid.

EXAMPLE 3

Preparation of 2,6-bis (2-Methylphenyl)-4-phenylphosphabenzene

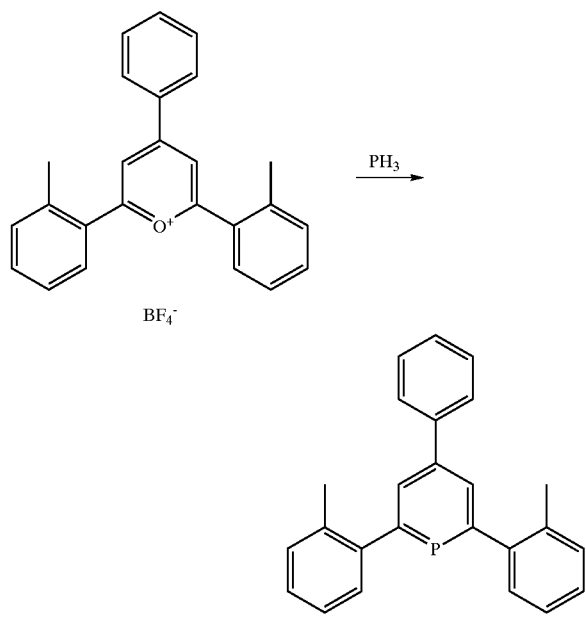

The reaction was carried out twice using 15 g (35 mmol) each time of 2,6-bis(2-methylphenyl)-4-phenylpyrylium tetrafluoroborate in 150 ml of n-butanol. The two autoclave products obtained after the reaction with $PH_3$ were combined and evaporated to about 50 ml under reduced pressure at about 80° C. The solid which precipitated was filtered off with suction, washed with n-pentane and subsequently dissolved in toluene. The toluene solution was then washed with water until the aqueous phase was neutral. After removal of the solvent, the residue was suspended in methanol, and dichloromethane was then added until the solid had completely dissolved. The resulting solution was evaporated under reduced pressure at about 40° C. until a solid precipitated. The solid was filtered off with suction, washed with a little n-pentane and subsequently dried in a high vacuum. Yield: 15.6 g (63%) of white solid.

EXAMPLE 4

Preparation of 2,6-bis(2,4,5-Trimethylphenyl)-4-phenylphosphabenzene

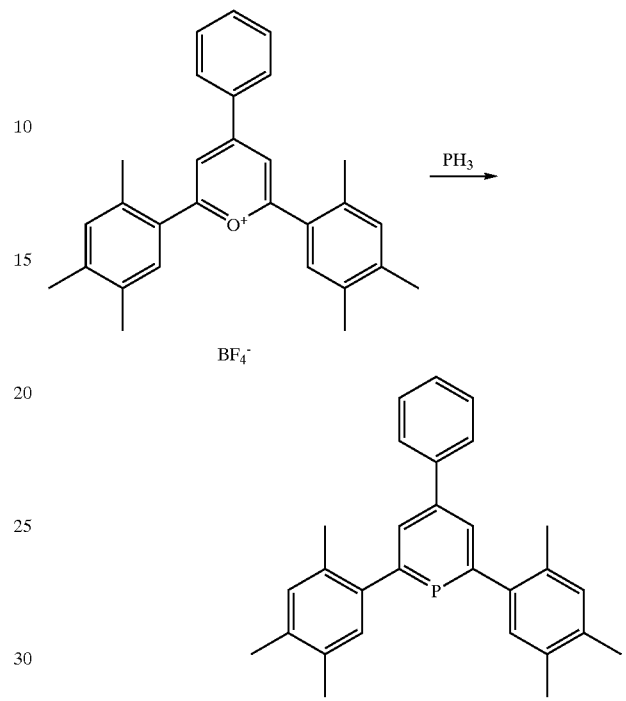

2.1 g (4.4 mmol) of 2,6-bis(2,4,5-trimethylphenyl)-4-phenylpyrylium tetrafluoroborate in 150 ml of n-butanol were used as starting material. The autoclave product obtained after the reaction with $PH_3$ was evaporated to about 50 ml under reduced pressure at about 80° C. The solid which precipitated was filtered off with suction, washed with n-pentane and subsequently dissolved in toluene. The toluene solution was then washed with water until the aqueous phase was neutral. After removing the solvent and washing with a little n-pentane, the residue was dissolved in dichloromethane. The resulting solution was diluted with methanol and then evaporated under reduced pressure at 30° C. until a solid precipitated. The solid was filtered off with suction, washed with a little n-pentane and subsequently dried in a high vacuum. Yield: 0.8 g (45%) of light-yellow solid.

EXAMPLE 5

Preparation of 10-Phenyl-1,2,7,8-dibenzo-3,4,5,6-tetrahydro-9-phosphaanthracene

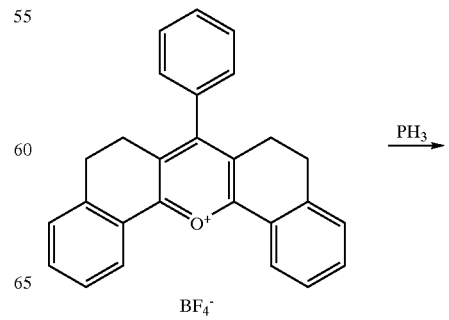

-continued

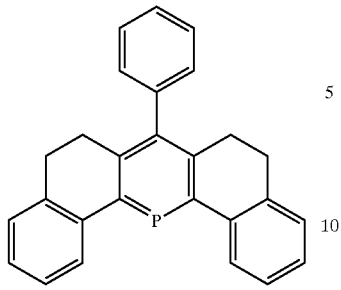

3.5 g (7.8 mmol) of 10-phenyl-1,2,7,8-dibenzo-3,4,5,6-tetrahydro-9-oxoniaanthracene tetrafluoroborate in 150 ml of ethanol were used as starting material. The autoclave product obtained after the reaction with $PH_3$ was freed of volatile constituents under reduced pressure at about 80° C. The orange residue was suspended in about 200 ml of warm toluene and immediately filtered through a frit. The toluene solution was then washed with water until the aqueous phase was neutral. After removing the solvent at 80° C. under reduced pressure, the solid which remained was dissolved in about 30 ml of methanol and about 200 ml of dichloromethane and then slowly evaporated under reduced pressure at 50° C. until a solid precipitated. The solid was filtered off with suction, washed with a little n-pentane and subsequently dried in a high vacuum. Yield: 0.7 g (24%) of light-yellow solid.

General Experimental Description for the Hydroformylation

Rhodium precursor, ligand and solvent were mixed under nitrogen in a Schlenk tube. The solution obtained was transferred to a 100 ml autoclave (material: HC) which had been flushed with $CO/H_2$ (1:1). The autoclave was pressurized cold with 5 bar of $CO/H_2$ (1:1). The reaction mixture was heated to the desired temperature over a period of 30 minutes while stirring vigorously with a sparging stirrer. The olefin used was then injected into the autoclave via a lock using a $CO/H_2$ pressure. The desired reaction pressure was then set immediately by means of $CO/H_2$ (1:1). During the reaction, the pressure in the reactor was maintained at the desired level by injection of further $CO/H_2$ via a pressure regulator. After the reaction time, the autoclave was cooled, vented and emptied. An analysis of the reaction mixture was carried out by means of GC using an internal standard and correction factor.

EXAMPLE 6

Low-pressure Hydroformylation of 1-Octene

Use of 2.2 mg of dicarbonylrhodium acetylacetonate (0.009 mmol), 53.9 mg (0.142 mmol) of 2,6-bis(2,4-dimethylphenyl)-4-phenylphosphabenzene from Example 2, 6.0 g (54 mmol) of 1-octene and 6.0 g of toluene at 90° C., 10 bar of $CO/H_2$ and a reaction time of 4 hours as described in the general experimental procedure gave a 1-octene conversion of 100%. The yield of nonanals was 91%, the selectivity to n-nonanal (n fraction) was 44% and the selectivity to n-nonanal and 2-methyloctanal ($\alpha$ fraction) was 80%.

EXAMPLE 7

Low-pressure Hydroformylation of 1-Octene

Use of 1.6 mg of dicarbonylrhodium acetylacetonate (0.006 mmol), 44.5 mg (0.125 mmol) of 2,6-bis(2-methylphenyl)-4-phenylphosphabenzene from Example 3, 5.9 g (53 mmol) of 1-octene and 5.8 g of toluene at 90° C., 10 bar of $CO/H_2$ and a reaction time of 4 hours as described in the general experimental procedure gave a 1-octene conversion of 99%. The yield of nonanals was 70%, the selectivity to n-nonanal (n fraction) was 44% and the selectivity to n-nonanal and 2-methyloctanal ($\alpha$ fraction) was 81%.

EXAMPLE 8

Low-pressure Hydroformylation of 1-Octene

Use of 1.5 mg of dicarbonylrhodium acetylacetonate (0.006 mmol), 46.9 mg (0.125 mmol) of 10-phenyl-1,2,7,8-dibenzo-3,4,5,6-tetrahydro-9-phosphaanthracene from Example 5, 5.9 g (53 mmol) of 1-octene and 6.0 g of toluene at 90° C., 10 bar of $CO/H_2$ and a reaction time of 4 hours as described in the. general experimental procedure gave a 1-octene conversion of 57%. The yield of nonanals was 3%, the selectivity to n-nonanal (n fraction) was 73% and the selectivity to n-nonanal and 2-methyloctanal ($\alpha$ fraction) was 100%.

EXAMPLE 9

Low-pressure Hydroformylation of 1-Octene

Use of 1.7 mg of dicarbonylrhodium acetylacetonate (0.007 mmol), 52.0 mg (0.127 mmol) of 2,6-bis(2,4,5-trimethylphenyl)-4-phenylphosphabenzene from Example 4, 5.8 g (52 mmol) of 1-octene and 6.0 g of toluene at 90° C., 10 bar of $CO/H_2$ and a reaction time of 4 hours as described in the general experimental procedure gave a 1-octene conversion of 100%. The yield of nonanals was 89%, the selectivity to n-nonanal (n fraction) was 43% and the selectivity to n-nonanal and 2-methyloctanal ($\alpha$ fraction) was 80%.

EXAMPLE 10

Intermediate-pressure Hydroformylation of Octene-N2

Use of 6.5 mg of dicarbonylrhodium acetylacetonate (0.025 mmol), 201.2 mg (0.493 mmol) of 2,6-bis(2,4,5-10 trimethylphenyl)-4-phenylphosphabenzene from Example 4, 23.4 g (209 mmol) of octene-N2 and 23.7 g of Texanol® at 100° C. and 60 bar of $CO/H_2$ as described in the general experimental procedure gave an octene-N2 conversion of 76% after a reaction time of 4 hours and 93% after a reaction time of 24 hours. The yield of nonanals was 76% after a reaction time of 4 hours and 93% after a reaction time of 24 hours.

General Experimental Description for Examination of the Degradation Behavior of Phosphabenzenes Under Hydroformylation Conditions Rhodium precursor, ligand, 1-octene and nonanal were mixed under nitrogen in a Schlenk tube. The solution obtained was transferred to a 100 ml autoclave (material: HC) which had been flushed with $CO/H_2$ (1:1). The autoclave was pressurized cold with 10 bar of $CO/H_2$ (1:1). The reaction mixture was heated to 150° C. over a period of 30 minutes while stirring vigorously with a sparging stirrer. A reaction pressure of 60 bar was then set by means of $CO/H_2$ (1:1). During the reaction, the pressure in the reactor was maintained at the desired level by injection of further $CO/H_2$ via a pressure regulator. After a reaction time of 3 days, the autoclave was cooled, vented and emptied under inert gas. The phosphabenzene degradation was quantified by means of GC using an NP-specific detector and, in selected cases, additionally by quantitative $^{31}$P-NMR spectroscopy.

EXAMPLE 11 (Comparison)

Degradation Behavior of 2,4,6-Triphenylphosphabenzene

Use of 7.3 mg of dicarbonylrhodium acetylacetonate (0.028 mmol), 160.0 mg (0.494 mmol) of 2,4,6-triphenylphosphabenzene, 12.0 g (107 mmol) of 1-octene and 12.0 g (85 mmol) of isononanal as described in the general experimental procedure gave a phosphabenzene degradation of 70% (GC) and 80% ($^{31}$P-NMR spectroscopy).

EXAMPLE 12 (Comparison)

Degradation Behavior of 2,3,5,6-Tetraphenylphosphabenzene

Use of 5.2 mg of dicarbonylrhodium acetylacetonate (0.020 mmol), 118.0 mg (0.295 mmol) of 2,3,5,6-tetraphenylphosphabenzene, 8.6 g (77 mmol) of 1-octene and 8.6 g (61 mmol) of isononanal as described in the general experimental procedure gave a phosphabenzene degradation of 47% (GC).

EXAMPLE 13 (Comparison)

Degradation Behavior of 2,3,4,5,6-Pentaphenylphosphabenzene

Use of 1.3 mg of dicarbonylrhodium acetylacetonate (0.005 mmol), 37.0 mg (0.078 mmol) of 2,3,4,5,6-pentaphenylphosphabenzene, 6.0 g (54 mmol) of 1-octene and 6.0 g (43 mmol) of isononanal as described in the general experimental procedure gave a phosphabenzene degradation of 60% (GC).

EXAMPLE 14 (Comparison)

Degradation Behavior of 2,6-bis(2-Naphthyl)-4-phenylphosphabenzene

Use of 8.1 mg of dicarbonylrhodium acetylacetonate (0.031 mmol), 153.3 mg (0.361 mmol) of 2,6-bis(2-naphthyl)-4-phenylphosphabenzene, 14.0 g (125 mmol) of 1-octene and 14.0 g (98 mmol) of isononanal as described in the general experimental procedure gave a phosphabenzene degradation of 54% (GC).

EXAMPLE 15

Degradation Behavior of 2,6-bis(2,4-Dimethylphenyl)-4-phenylphosphabenzene

Use of 7.3 mg of dicarbonylrhodium acetylacetonate (0.028 mmol), 167.1 mg (0.439 mmol) of 2,6-bis(2,4-dimethylphenyl)-4-phenylphosphabenzene, 12.0 g (107 mmol) of 1-octene and 12.0 g (84 mmol) of isononanal as described in the general experimental procedure gave a phosphabenzene degradation of 5% (GC).

EXAMPLE 16

Degradation Behavior of 2,6-bis (2-Methylphenyl)-4-phenylphosphabenzene

Use of 7.3 mg of dicarbonylrhodium acetylacetonate (0.028 mmol), 165.0 mg (0.460 mmol) of 2,6-bis(2-methylphenyl)-4-phenylphosphabenzene, 12.0 g (107 mmol) of 1-octene and 12.0 g (84 mmol) of isononanal as described in the general experimental procedure gave a phosphabenzene degradation of 14% (GC).

EXAMPLE 17

Degradation Behavior of 2,6-bis(2,4,5-Trimethylphenyl)-4-phenylphosphabenzene

Use of 3.1 mg of dicarbonylrhodium acetylacetonate (0.012 mmol), 94.8 mg (0.232 mmol) of 2,6-bis(2,4,5-trimethylphenyl)-4-phenylphosphabenzene, 6.0 g (54 mmol) of 1-octene and 6.0 g (42 mmol) of isononanal as described in the general experimental procedure gave a phosphabenzene degradation of 19% (GC) and 40% ($^{31}$P-NMR spectroscopy).

We claim:

1. A phosphabenzene compound of the formula (I)

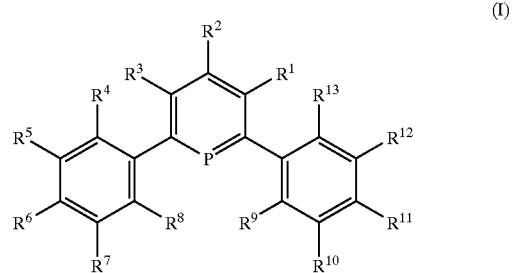

where the radicals $R^1$ to $R^{13}$ are, independently of one another, hydrogen, COOM, SO$_3$M, NR$_3$X, NR$_2$, OR, COOR or SR (where M=hydrogen, NH$_4$ or alkali metal, X=anion, R=hydrogen or C$_1$–C$_6$-alkyl), or C$_1$–C$_{12}$-alkyl, C$_6$–C$_{12}$-aryl, C$_7$–C$_{12}$-aralkyl, C$_7$–C$_{12}$-alkaryl or C$_3$–C$_6$-heteroaromatics, where the alkyl, aryl, alkaryl and aralkyl radicals optionally substituted by the abovementioned radicals as substituents and two or more of the radicals can optionally be joined to form aliphatic or fused-on rings, where at least one of the radicals $R^4$ and $R^8$ and at least one of the radicals $R^9$ and $R^{13}$ is not hydrogen.

2. A phosphabenzene compound as defined in claim 1, wherein at least one of the radicals $R^4$ and $R^8$ and at least one of the radicals $R^9$ and $R^{13}$ are, independently of one another, C$_1$–C$_{12}$-alkyl, C$_6$–C$_{12}$-aryl, C$_7$–C$_{12}$-aralkyl or C$_7$–C$_{12}$-alkaryl, or ($R^4$ and $R^3$) and/or ($R^{13}$ and $R^1$) form a C$_2$–C$_4$-alkylene radical.

3. A phosphabenzene compound as defined in claim 2, wherein at least one of the radicals $R^4$ and $R^8$ and at least one of the radicals $R^9$ and $R^{13}$ are, independently of one another, C$_1$–C$_6$-alkyl, or ($R^4$ and $R^3$) and ($R^{13}$ and $R^1$) in each case form a C$_2$–C$_3$-alkylene radical.

4. A phosphabenzene compound as defined in claim 1, wherein the radical $R^2$ is a phenyl radical which optionally may be substituted by from 1 to 5 C$_1$–C$_6$-alkyl radicals.

5. A phosphabenzene compound as defined in claim 1, wherein the radicals $R^1$ and $R^3$ are hydrogen and not more than 3 of the radicals $R^4$ to $R^8$ and $R^9$ to $R^{13}$ are other than hydrogen.

6. A process for preparing a compound of the formula (I) as defined in claim 1 by reacting a corresponding pyrylium salt with PH$_3$ in the presence or absence of a catalytic amount of acid or base and in the presence or absence of a solvent or diluent.

7. A process as defined in claim 6, wherein the pyrylium salt is brought into contact with PH$_3$ at above 0° C. and reacted at above 0° C.–200° C. and a pressure above 1 bar, with the reaction being carried out at a $PH_3$ partial pressure in the range from 0.1 to 100 bar.

8. A complex of a compound as defined in claim 1 with a metal of transition group VIII of the Periodic Table of the Elements.

9. A process for the hydroformylation of $C_2$–$C_{20}$-olefins by reaction with CO and $H_2$ in the presence of a complex as defined in claim 8 as catalyst at from 0 to 200° C. and a pressure in the range from 1 to 700 bar.

* * * * *